US008444972B2

(12) United States Patent
Rock et al.

(10) Patent No.: US 8,444,972 B2
(45) Date of Patent: May 21, 2013

(54) ANTITUMOR ANTIBODIES, PROTEINS, AND USES THEREOF

(75) Inventors: Kenneth L. Rock, Chestnut Hill, MA (US); Dancella Fernandes, Framingham, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 12/851,127

(22) Filed: Aug. 5, 2010

(65) Prior Publication Data

US 2011/0212022 A1 Sep. 1, 2011

Related U.S. Application Data

(60) Division of application No. 11/491,500, filed on Jul. 21, 2006, now Pat. No. 7,902,339, which is a continuation of application No. 10/747,031, filed on Dec. 23, 2003, now abandoned, which is a continuation of application No. 09/618,421, filed on Jul. 18, 2000, now Pat. No. 6,693,176.

(60) Provisional application No. 60/145,337, filed on Jul. 23, 1999.

(51) Int. Cl.
*A61K 39/395* (2006.01)

(52) U.S. Cl.
USPC .......... 424/130.1; 424/133.1; 424/138.1; 424/155.1; 424/174.1; 435/7.23; 530/350; 530/387.3; 530/387.7; 530/388.1; 530/388.8; 500/391.3

(58) Field of Classification Search ......... 424/155.1, 424/130.1, 133.1, 138.1, 174.1; 530/350, 530/387.3, 387.7, 388.1, 388.8, 391.3; 435/7.23
See application file for complete search history.

(56) References Cited

U.S. PATENT DOCUMENTS

| | | | |
|---|---|---|---|
| 5,104,652 A | 4/1992 | Houghton et al. |
| 5,576,423 A | 11/1996 | Aversa et al. |
| 5,618,920 A | 4/1997 | Robinson et al. |
| 5,688,657 A | 11/1997 | Tsang et al. |
| 5,756,096 A | 5/1998 | Newman et al. |
| 5,817,513 A | 10/1998 | Lopez et al. |
| 5,830,470 A | 11/1998 | Nakamura et al. |
| 5,939,532 A | 8/1999 | Nakamura et al. |
| 6,042,828 A | 3/2000 | Nakamura et al. |
| 6,075,181 A | 6/2000 | Kucherlapati et al. |
| 6,156,321 A | 12/2000 | Thorpe et al. |
| 6,180,370 B1 | 1/2001 | Queen et al. |
| 7,214,775 B2 | 5/2007 | Hanai et al. |
| 2006/0275307 A1 | 12/2006 | Fanger et al. |
| 2007/0031423 A1 | 2/2007 | Fanger et al. |

FOREIGN PATENT DOCUMENTS

| | | |
|---|---|---|
| EP | 0267615 A2 | 5/1988 |
| EP | 0369425 A1 | 5/1990 |
| EP | 0882794 A2 | 12/1998 |
| WO | 01/07481 A1 | 2/2001 |
| WO | 01/91793 A1 | 12/2001 |

OTHER PUBLICATIONS

Wu, Herren et al., "Humanization of a Murine Monoclonal Antibody by Simultaneous Optimization of Framework and CDR Residues," J. Mol. Biol., vol. 294:151-162 (1999).
Yamaguchi, Hiroshi et al., "Human monoclonal antibody and dual GM2/GD2 specificity derived from an immunized melanoma patient," Proc. Natl. Acad. Sci. USA, vol. 87:3333-3337 (1990).
Zhang, Shengle et al., "Selection of Tumor Antigens as Targets for Immune Attack Using Immunohistochemistry: I. Focus on Gangliosides," Int. J. Cancer, vol. 73:42-49 (1997).
Norwegian office action for Application No. 2002 0329, dated Oct. 16, 2008.
Dillman, Robert O., "Monoclonal Antibody Therapy for Lymphoma," Cancer Practice, vol. 9(2):71-80 (2001).
Irie, Reiko F. et al., "Human antibody of OFA-I, a tumor antigen, produced in vitro by Epstein-Barr virus-transformed human B-lymphoid cell lines," Proc. Natl. Acad. Sci. USA, vol. 79:5666-5670 (1982).
Magnani, John L. et al., "A Monosialoganglioside Is a Monoclonal Antibody-Defined Antigen of Colon Carcinoma," Science, vol. 212:55-56 (1981).
Orlandi, Rosaria et al., "Cloning immunoglobulin variable domains for expression by the polymerase chain reaction," Proc. Natl. Acad. Sci. USA, vol. 86:3833-3837 (1989).
Vrionis, Fotios D. et al., "Five New Epitope-defined Monoclonal Antibodies Reactive with GM2 and Human Glioma and Medulloblastoma Cell Lines," Cancer Research, vol. 49:6645-6651 (1989).
Zhao, Yunfeng et al., "Endowing self-binding feature restores the activities of a loss-of-function chimerized anti-GM2 antibody," Cancer Immunol. Immunother., vol. 56:147-154 (2007).
Bergers, Gabriele et al., "Extrinsic regulators of epithelial tumor progression: metalloproteinases," Current Opinion in Genetics & Development, vol. 10:120-127 (2000).
Bernard, Alain et al., "A Unique Epitope on the CD2 Molecule Defined by the Monoclonal Antibody 9-1: Epitope-Specific Modulation of the E-Rosette Receptor and Effects on T-Cell Functions," Human Immunology, vol. 17:388-405 (1986).
Bodey, Bela et al., "Failure of Cancer Vaccines: The Significant Limitations of this Approach to Immunotherapy," Anticancer Research, vol. 20:2665-2676 (2000).
Boyer, Cinda M. et al., "Relative Cytotoxic Activity of Immunotoxins Reactive with Different Epitopes on the Extracellular Domain of the c-erbB-2 (HER-2/neu) Gene Product p185," Int. J. Cancer, vol. 82:525-531 (1999).
Caldas, Cristina et al., "Humanization of the anti-CD18 antibody 6.7: an unexpected effect of a framework residue in binding to antigen," Molecular Immunology, vol. 39:941-952 (2003).
Campbell, Peter et al., "Monoclonal antibody therapy for lymphoma," Blood Reviews, vol. 17:143-152 (2003).

(Continued)

*Primary Examiner* — Stephen Rawlings
(74) *Attorney, Agent, or Firm* — Nelson Mullins Riley & Scarborough LLP; Debra J. Milasincic, Esq.

(57) ABSTRACT

Antibodies that bind to a 40 kDa protein which is expressed on tumors, but is not expressed on normal adult hemopoietic cells are disclosed. Also disclosed are methods for production and the use of such antibodies.

19 Claims, 5 Drawing Sheets

OTHER PUBLICATIONS

Casset, Florence et al., "A peptide mimetic of an anti-CD4 monoclonal antibody by rational design," Biochemical and Biophysical Research Communications, vol. 307:198-205 (2003).

Chen, Yvonne et al., "Selection and Analysis of an Optimized Anti-VEGF Antibody: Crystal Structure of an Affinity-matured Fab in Complex with Antigen," J. Mol. Biol., vol. 293:865-881 (1999).

Chien, Nadine C. et al., "Significant structural and functional change of an antigen-binding site by a distant amino acid sibstitution: Proposal of a structural mechanism," Proc. Natl. Acad. Sci. USA, vol. 86:5532-5536 (1989).

De Pascalis, Roberto et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, vol. 169:3076-3084 (2002).

De Santes, Kenneth et al., "Radiolabeled Antibody Targeting of the HER-2/neu Oncoprotein," Cancer Research, vol. 52:1916-1923 (1992).

Fernandes, Dancella M. et al., "A Monoclonal Antibody Reactive with a 40-kDa Molecule on Fetal Thymocytes and Tumor Cells Blocks Proliferation and Stimulates Aggregation and Apoptosis," The Journal of Immunology, vol. 163:1306-1314 (1999).

Giusti, Angela M. et al., "Somatic diversification of S107 from an antiphosphocholine to an anti-DNA autoantibody is due to a single base change in its heavy chain variable region," Proc. Natl. Acad. Sci. USA, vol. 84:2926-2930 (1987).

Greenspan, Neil S. et al., "Defining epitopes: It's not as easy as it seems," Nature Biotechnology, vol. 17:936-937 (1999).

Gura, Trisha, "Systems for Identifying New Drugs Are Often Faulty," Science, vol. 278(5340):1041-1042 (1997).

Guessow, Detlef et al., "Humanization of monoclonal antibodies," Methods in Enzymology, vol. 203:99-121 (1991).

Hanibuchi, Masaki et al., "Therapeutic Efficacy of Mouse-Human Chimeric Anti-ganglioside GM2 Monoclonal Antibody Against Multiple Organ Micrometastases of Human Lung Cancer in NK Cell-depleted SCID Mice," Int. J. Cancer, vol. 78:780-485 (1998).

Hellstrom, Ingegerd et al., "Strong antitumor activities of IgG3 antibodies to a human melanoma-associated ganglioside," Proc. Natl. Acad. Sci. USA, vol. 82:1499-1502 (1985).

Holm, Patrik et al., "Functional mapping and single chain construction of the anti-cytokeratin 8 monoclonal antibody TS1," Molecular Immunology, vol. 44:1075-1084 (2007).

Jiang, Beihai et al., "A Novel Peptide Isolated from a Phage Display Peptide Library with Trastuzumab Can Mimic Antigen Epitope of HER-2," The Journal of Biological Chemistry, vol. 280(6):4656-4662 (2005).

Kasai, Masataka et al., "A New Differentiation Antigen (FT-1) Shared with Fetal Thymocytes and Leukemic Cells in the Mouse," J. Exp. Med., vol. 159:971-980 (1983).

Kim, Kwang-Mi et al., "Both the Epitope Specificity and Isotype are Important in the Antitumor Effect of Monoclonal Antibodies Against HER-2/neu Antigen," Int. J. Cancer, vol. 102:428-434 (2002).

Kipps, Thomas J. et al., "Importance of Immunoglobulin Isotype in Human Antibody-dependent, Cell-mediated Cytotoxicity Directed by Murine Monoclonal Antibodies," J. Exp. Med., vol. 161:1-17 (1985).

Lewis, G.D. et al., "Differential responses of human tumor cell lines to anti-p185HER2 monoclonal antibodies," Cancer Immunol. Immunother., vol. 37(4):255-263 (1993).

Lewis, Gail D. et al., "Growth Regulation of Human Breast and Ovarian Tumor Cells by Heregulin: Evidence for the Requirement of ErbB2 as a Critical Component in Mediating Heregulin Responsiveness," Cancer Research, vol. 56:1457-1465 (1996).

MacCallum, Robert M. et al., "Antibody-antigen Interactions: Contact Analysis and Binding Site Topography," J. Mol. Biol., vol. 262:732-745 (1996).

Malard, Veronique et al., "21.1.1, A Novel Activation Marker of T and B Cells," Molecular Immunology, vol. 28 (4/5):417-426 (1991).

Mariuzza, R.A. et al., "The Structural Basis of Antigen-Antibody Recognition," Ann. Rev. Biophys. Biophys. Chem., vol. 16:139-159 (1987).

Masui, Hideo et al., "Mechanism of Antitumor Activity in Mice for Anti-Epidermal Growth Factor Receptor Monoclonal Antibodies with Different Isotypes," Cancer Research, vol. 46:5592-5598 (1986).

Mountain, A. et al., "Engineering Antibodies for Therapy," Biotechnology & Genetic Engineering Reviews, vol. 10, Michael P. Tombs Ed., pp. 1-143 (1992).

Mueller, Barbara M. et al., "Expression of tissue factor by melanoma cells promotes efficient hematogenous metastasis," Proc. Natl. Acad. Sci. USA, vol. 89:11832-11836 (1992).

O'Boyle, Kevin P. et al., "Patterns of Ganglioside Expression in B Cell Neoplasms," Leukemia and Lymphoma, vol. 21:255-266 (1996).

Pettersen, Rolf D. et al., "CD47 Signals T Cell Death," The Journal of Immunotherapy, vol. 162:7031-7040 (1999).

Pinto, Valerian B. et al., "Characterization of the Proliferative Response of CD4-8-Thymic T Lymphoma Cell Line to Stimulation by Thymic Cellular Elements," The Journal of Immunology, vol. 147:42-49 (1991).

Press, Oliver W. et al., "Ricin A-chain Containing Immunotoxins Directed Against Different Isotopes on the CD2 Molecule Differ in Their Ability to Kill Normal and Malignant T Cells," The Journal of Immunology, vol. 141 (12):4410-4417 (1988).

Reichert, Roger A. et al., "Ontogeny of Lymphocyte Homing Receptor Expression in the Mouse Thymus," The Journal of Immunology, vol. 136(10):3535-3542 (1986).

Retter, Marc W. et al., "Characterization of a Proapoptotic Antiganglioside GM2 Monoclonal Antibody and Evaluation of Its Therapeutic Effect on Melanoma and Small Cell Lung Carcinoma Xenografts," Cancer Res., vol. 65 (14):6425-6434 (2005).

Riemer, Angelika B. et al., "Matching of trastuzumab (Herceptina) epitope mimics onto the surface of Her-2/neu—a new method of epitope definition," Molecular Immunology, vol. 42:1121-1124 (2005).

Rudikoff, Stuart et al., "Single amino acid substitution altering antigen-binding specificity," Proc. Natl. Acad. Sci. USA, vol. 79:1979-1983 (1982).

Saito, Masaki et al., "Distinctive Characteristics of Ganglioside-Profiles in Human Leukemia-Lymphoma Cell Lines," New Vistas in Glycolipid Research, Akira Makita ed., Plenum Press, pp. 369-391 (1982).

Stancovski, Ilana et al., "Mechanistic aspects of the opposing effects of monoclonal antibodies to the ERBB2 receptor on tumor growth," Proc. Natl. Acad. Sci. USA, vol. 88:8691-8695 (1991).

Stobel, Thomas et al., "b1-Integrins Partly Mediate Binding of Ovarian Cancer Cells to Peritoneal Mesothelium in Vitro," Gynecologic Oncology, vol. 73:362-367 (1999).

Tai, Tadashi et al., "Ganglioside GM2 as a human tumor antigen (OFA-I-1)," Proc. Natl. Acad. Sci. USA, vol. 80:5392-5396 (1983).

Takashi, Tohru et al., "FT-2 Antigen for Distinguishing Lymphocyte Subpopulations in the Developing Thymus," Immunology Letters, vol. 9:259-262 (1985).

Takei, Fumio, "A Novel Differentiation Antigen on Proliferating Murine Thymocytes Identified by a Rat Monoclonal Antibody," The Journal of Immunology, vol. 132(2):766-771 (1984).

Tockman, Melvyn S. et al., "Considerations in Bringing a Cancer Biomarker to Clinical Application," Cancer Research, vol. 52(Suppl.):2711s-2718s (1992).

Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).

Vitetta, Ellen S. et al., "Monoclonal Antibodies as Agonists: An Expanded Role for Their Use in Cancer Therapy," Cancer Research, vol. 54:5301-5309 (1994).

Vuist, Wim M.J. et al., "Two Distinct Mechanisms of Antitumor Activity Mediated by the Combination of Interleukin 2 and Monoclonal Antibodies," Cancer Research, vol. 50:5767-5772 (1990).

Warren, Andrew P. et al., "CD98: A Type II Transmembrane Glycoprotein Expressed From the Beginning of Primitive and Definitive Hematopoiesis May Play a Critical Role in the Development of Hematopoietic Cells," Blood, vol. 87(9):3676-3687 (1996).

Kasai, Masataka et al., "Two New Fetal Thymocyte Antigens, FT-1 and FT-2," Immunological Reviews, vol. 82:105-115 (1984).

Brazilian Office Action for Application No. PI0012704-3, pp. 1-3.

Miyake, Masayuki et al., "Generation of Two Murine Monoclonal Antibodies That Can Discriminate N-Glycolyl and N-Acetyl Neuraminic Acid Residues of GM2 Gangliosides," Cancer Research, vol. 48:6154-6160 (1988).

Nakamura, Kazuyasu et al., "Chimeric Anti-Ganglioside GM2 Antibody with Antitumor Activity," Cancer Research, vol. 54:1511-1516 (1994).

Nakamura, Kazuyasu et al., "Dissection and optimization of immune effector functions of humanization anti-ganglioside GM2 monoclonal antibody," Molecular Immunology, vol. 37:1035-1046 (2000).

Natoli, Edward J., Jr. et al., "A Murine Monoclonal Antibody Detecting N-Acetyl- and N-Glycolyl-GM2: Characterization of Cell Surface Reactivity," Cancer Research, vol. 46:4116-4120 (1986).

Nishinaka, Yumiko et al., "Development of a Human Monoclonal Antibody to Ganglioside GM2 with Potential for Cancer Treatment," Cancer Research, vol. 56:5666-5671 (1996).

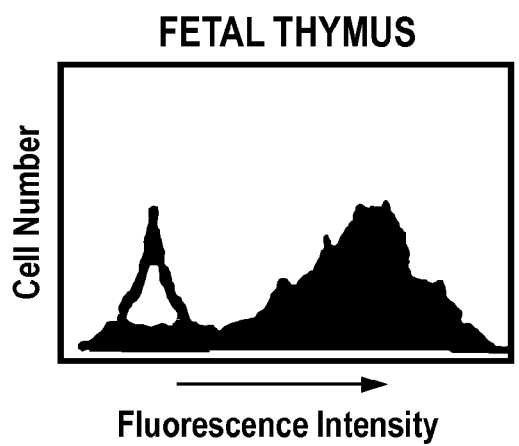
Fig. 2A — FETAL THYMUS
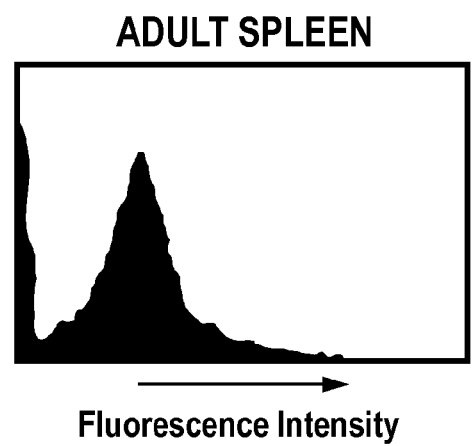
Fig. 2B — ADULT SPLEEN
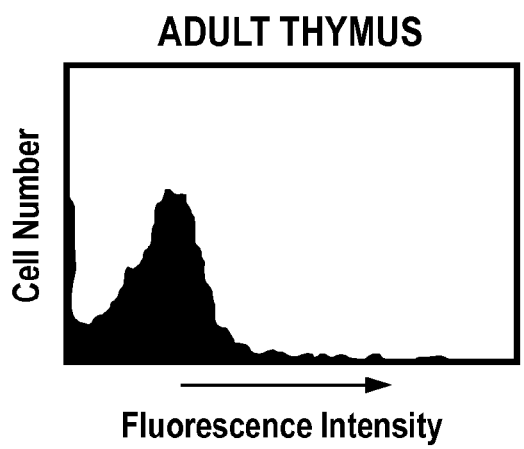
Fig. 2C — ADULT THYMUS
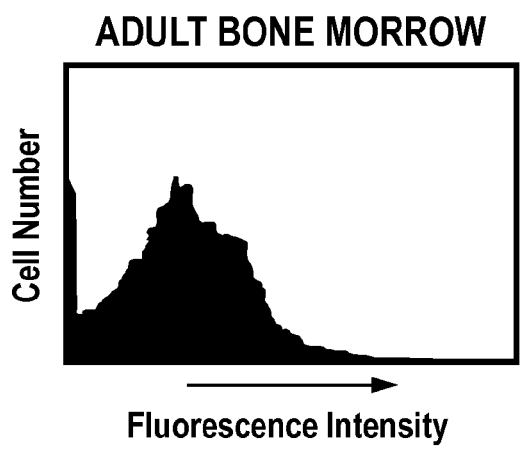
Fig. 2D — ADULT BONE MORROW

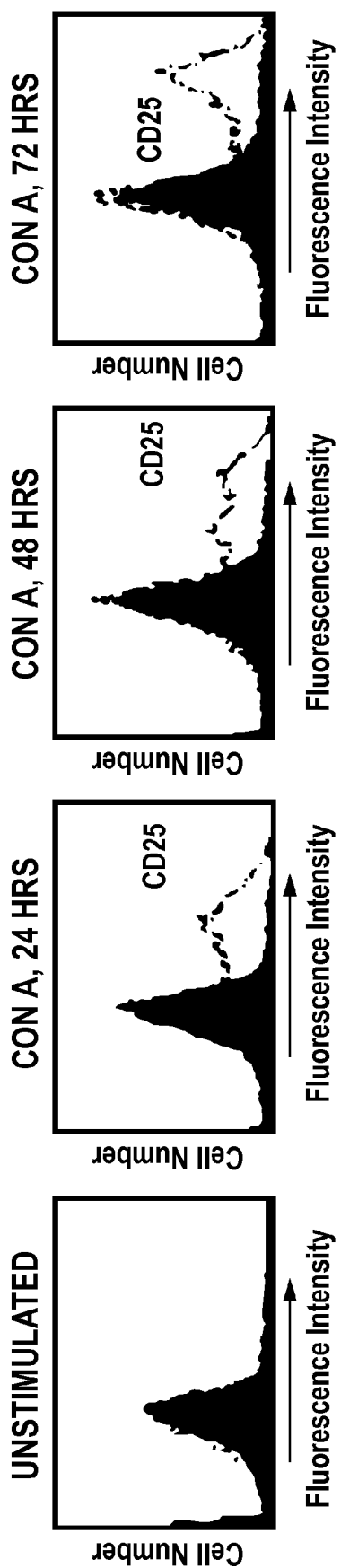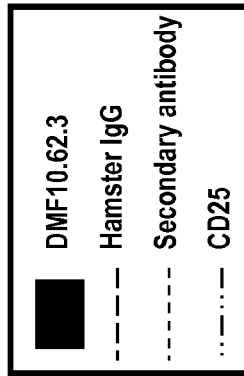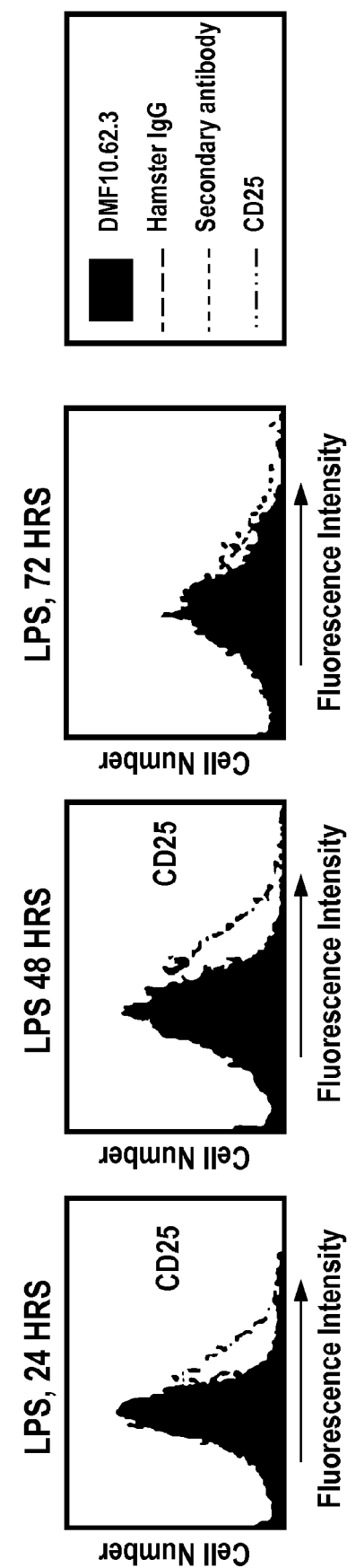
Fig. 3A Fig. 3B Fig. 3C Fig. 3D Fig. 3E Fig. 3F Fig. 3G

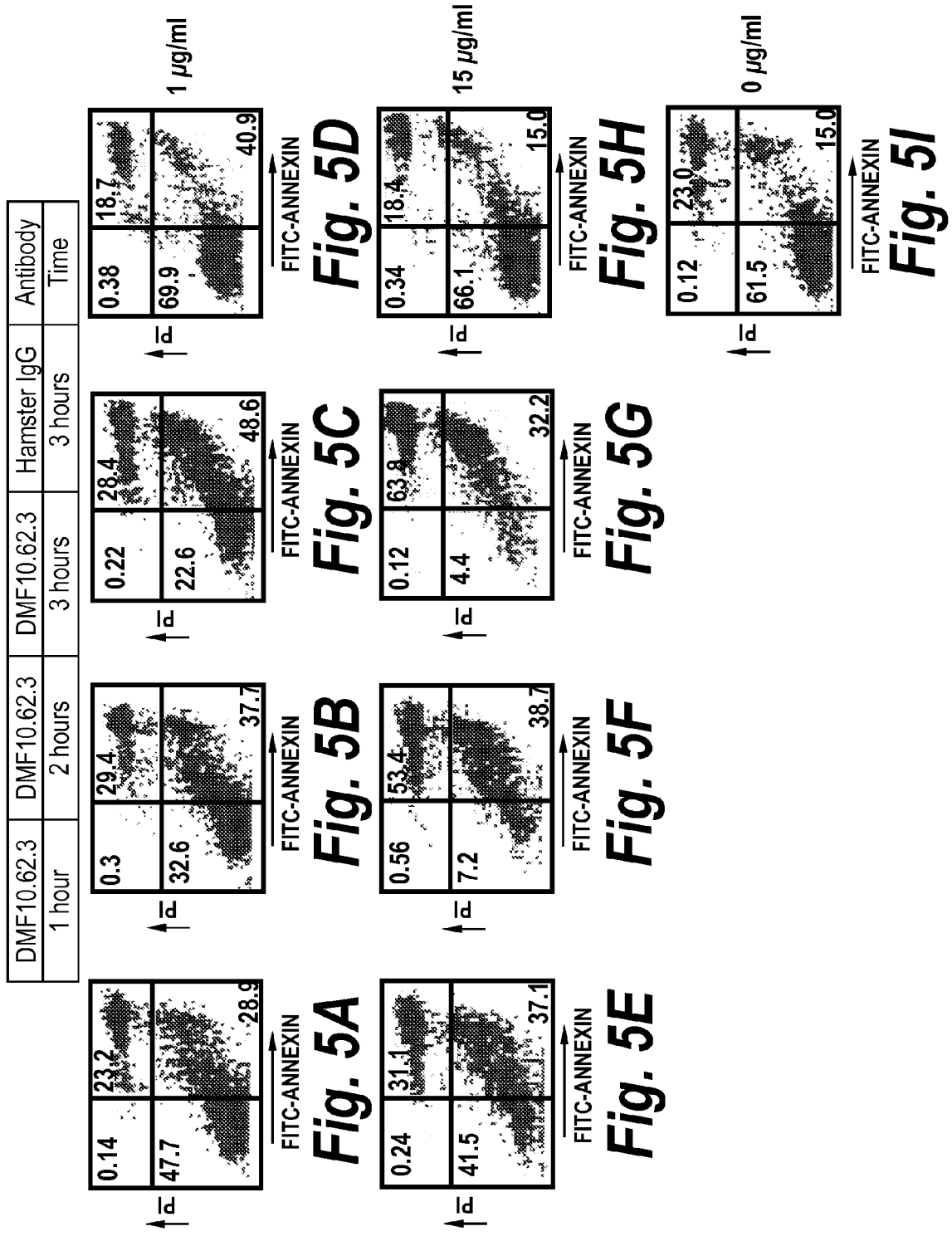

ANTITUMOR ANTIBODIES, PROTEINS, AND USES THEREOF

STATEMENT OF RELATED APPLICATIONS

This application is a divisional of U.S. patent application Ser. No. 11/491,500, filed Jul. 21, 2006, (now U.S. Pat. No. 7,902,339, issued Mar. 8, 2011); which is a continuation of U.S. application Ser. No. 10/747,031, filed Dec. 23, 2003, (now abandoned), which is a continuation of U.S. application Ser. No. 09/618,421, filed Jul. 18, 2000, (now U.S. Pat. No. 6,693,176), which, in turn, claims priority to U.S. Provisional Patent Application Ser. No. 60/145,337, filed Jul. 23, 1999. The contents of all of the aforementioned patents and patent applications are incorporated herein by reference.

STATEMENT AS TO FEDERALLY SPONSORED RESEARCH

This invention was made with Government support under grant number R01CA55233-06, awarded by the National Institutes of Health. The Government has certain rights in the invention.

FIELD OF THE INVENTION

The present invention relates to antibodies and the proteins to which they specifically bind, and to methods for production and the use of such antibodies that specifically bind to tumor cells.

BACKGROUND OF THE INVENTION

The E710.2.3 cell line is a cloned murine CD4-CD8-thymic T lymphoma cell line, originally isolated from a thymic tumor of an AKR/J mouse. When cultured by itself at low density, E710.2.3 does not proliferate spontaneously, unless it is stimulated with phorbol 12-myristate 13-acetate (PMA). E710.2.3 can be stimulated to proliferate by contact with thymocytes or splenocytes. However, E710.2.3 can proliferate spontaneously when cultured at high density in the absence of PMA or other cells. When E710.2.3 is injected into syngeneic mice it grows as a malignant tumor in lymphoid organs and the thymus.

SUMMARY OF THE INVENTION

The invention is based on the discovery of monoclonal antibodies that can specifically bind to a 40 kDa protein expressed on the surface of numerous types of tumor cells, but do not bind to adult normal hematopoietic cells. The new monoclonal antibodies can block proliferation and induce apoptosis of tumor cells to which they specifically bind.

Based on these discoveries, the invention features monoclonal antibodies, or antigen-binding fragments thereof, wherein the monoclonal antibodies (a) bind to fetal thymocytes, (b) inhibit cell proliferation of a cell upon binding to the cell, and (c) do not bind to adult thymocytes. The monoclonal antibodies can also induce homotypic aggregation upon binding to a cell, induce apoptosis in a cell to which they bind, and can specifically bind to one or more tumor cell lines in the group E710.2.3, RMA-S, CTLL, LB 17.4, A20, WEHI-231, PBK101A2, C2.3, B16, MC57, WOP-3027, 293T, 143Btk, Jurkat, and Cos. The antibodies can be labeled, e.g., with a detectable label.

Also within the invention is the monoclonal antibody DMF10.62.3 produced by the hybridoma cell line ATCC No. PTA-377, the monoclonal antibody DMF 10.167.4 produced by the hybridoma cell line ATCC No. PTA-405, and the monoclonal antibody DMF10.34.36 produced by the hybridoma cell line ATCC No. PTA-404.

The invention also features monoclonal antibodies, that bind to the same protein as the protein bound by the monoclonal antibody produced by hybridoma cell line ATCC No. PTA-377, hybridoma cell line ATCC No. PTA-405, or hybridoma cell line ATCC No. PTA-404. The monoclonal antibody can be humanized.

In another aspect, the invention features monoclonal antibodies, or antigen-binding fragments thereof, that bind specifically to a 40 kDa protein bound by the monoclonal antibody produced by hybridoma cell line ATCC No. PTA-377, hybridoma cell line ATCC No. PTA-405, or hybridoma cell line ATCC No. PTA-404.

In yet another aspect, the invention features chimeric monoclonal antibodies, or antigen-binding fragments thereof, that bind to the same protein as the protein bound by the monoclonal antibody produced by hybridoma cell line ATCC No. PTA-377, hybridoma cell line ATCC No. PTA-405, or hybridoma cell line ATCC No. PTA-404, wherein the chimeric antibodies include non-human variable regions and human constant regions of light and heavy chains.

In still another aspect, the invention features monoclonal antibodies, or antigen-binding fragments thereof, that bind to the same epitope as the epitope bound by the monoclonal antibody produced by hybridoma cell line hybridoma cell line ATCC No. PTA-377, hybridoma cell line ATCC No. PTA-405, or hybridoma cell line ATCC No. PTA-404.

The invention also features monoclonal antibodies, or antigen-binding fragments thereof, that bind specifically to a protein characterized by (i) a molecular weight of 40 kDa, (ii) expression on the surface of fetal thymocytes, (iii) no expression on the surface of adult thymocytes, (iv) the ability to block cell proliferation upon binding by the antibody, and (v) the ability to induce homotypic aggregation upon binding by the antibody. The monoclonal antibody binds specifically to a protein that is further characterized by (vi) the ability to induce apoptosis in a cell upon binding by the antibody, and (vii) expression on the surface of a group of tumor cell lines consisting of E710.2.3, RMA-S, CTLL, LB 17.4, A20, WEHI-231, PBK101A2, C2.3, B16, MC57, WOP-3027, 293T, 143Btk, Jurkat, and Cos.

The invention further features an antigen-binding fragments of the monoclonal antibodies described herein. The antigen binding fragments can be labeled, e.g., with a detectable label.

The invention also features the hybridoma cell lines that produce the monoclonal antibodies described herein. For example, the invention features the hybridoma cell line ATCC No. PTA-377, hybridoma cell line ATCC No. PTA-405, or hybridoma cell line ATCC No. PTA404.

The invention further features a substantially pure protein characterized by (i) a molecular weight of 40 kDa, (ii) expression on the surface of fetal thymocytes, (iii) no expression on the cell surface of adult thymocytes, (iv) the ability to block cell proliferation upon binding by the antibody described herein, and (v) the ability to induce homotypic aggregation upon binding by the antibody described herein. The protein can be further characterized by (vi) expression on a group of tumor cell lines consisting of E710.2.3, RMA-S, CTLL, LB17.4, A20, WEHI-231, -PBK101A2, C2.3, B16, MC57, WOP-3027, 293T, 143Btk, Jurkat, and Cos, and (vii) the ability to induce apoptosis in a cell upon binding by the antibody described herein.

In another aspect, the invention features substantially pure proteins that bind to the monoclonal antibody produced by hybridoma cell line ATCC No. PTA-377, hybridoma cell line ATCC No. PTA405, or hybridoma cell line ATCC No. PTA404.

The invention also features a pharmaceutical composition comprising the monoclonal antibody described herein and a pharmaceutically acceptable carrier.

The invention further features a method for detecting a tumor cell in a subject. The method includes contacting a cell sample from the subject with one or more of the monoclonal antibodies described herein, and detecting binding of the antibody to the sample, wherein binding indicates the presence of a tumor cell in the subject. Examples of tumor cells include thymic lymphoma, T-cell tumor, a B-cell lymphoma, melanoma, osteosarcoma, and acute T-cell leukemia. The tumor cell may also be in a patient. The monoclonal antibodies used to detect tumors can be labelled.

The invention also features a method of inhibiting tumor cell proliferation. The method includes contacting the tumor cell with a quantity of the monoclonal antibodies described herein, sufficient to inhibit proliferation of the tumor cell.

In another embodiment, the invention features a method of inducing apoptosis in a cell. The method includes contacting the cell with a quantity of one or more of the monoclonal antibodies described herein sufficient to induce apoptosis in the cell. The cell can be a tumor cell selected from the group consisting of thymic lymphoma, T-cell tumor, a B-cell lymphoma, melanoma, osteosarcoma, and acute T-cell leukemia. The cell can be in vitro or in vivo.

The invention also encompasses a kit for tumor diagnosis, including one or more of the monoclonal antibodies described herein and instructions for its use. The kit can contain a tumor cell selected from the group consisting of thymic lymphoma, T cell tumor, a B-cell lymphoma, melanoma, osteosarcoma, and acute T cell leukemia.

The invention also includes a tumor cell targeting agent including one or more of the monoclonal antibodies described herein, which can be conjugated to a moiety to deliver the moiety to a tumor cell. Examples of moieties include anti-tumor agents, cytotoxins, cytokines, or reporter groups.

Another embodiment of the invention is a method of selectively delivering a moiety to a tumor cell in a mammal. The method includes administering to the mammal the targeting agent described herein linked to the moiety and allowing sufficient time for the targeting agent to reach the tumor cell wherein the antibody in the targeting agent binds to the tumor agent described herein linked to the moiety and allowing sufficient time for the targeting agent to reach the tumor cell wherein the antibody in the targeting agent binds to the tumor cell, thereby selectively delivering the moiety to the tumor cell in the mammal. Examples of moieties include antitumor agents, cytotoxins, cytokines, and reporter groups.

The invention further encompasses a method of isolating the 40 kDa protein described herein. The method includes contacting a sample containing the protein with the monoclonal antibodies described herein for a time and under conditions sufficient to enable the formation of monoclonal antibody/protein complexes, removing one or more of the complexes, if any, from the sample and removing the protein from the complex, thereby isolating the protein.

An "isolated nucleic acid sequence" is a nucleic acid sequence that is substantially free of the genes that flank the nucleic acid sequence in the genome of the organism in which it naturally occurs. The term therefore includes a recombinant nucleic acid sequence incorporated into a vector, into an autonomously replicating plasmid or virus, or into the genomic nucleic acid sequence of a prokaryote or eukaryote. It also includes a separate molecule such as a cDNA, a genomic fragment, a fragment produced by polymerase chain reaction (PCR), or a restriction fragment.

An antibody that "specifically binds" to a protein is one that binds to a protein, but which does not recognize and bind to other molecules in a sample, e.g., a biological sample, which naturally includes the protein, e.g., the 40 kDa protein.

"Conservative" amino acid substitutions are substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Any one of a family of amino acids can be used to replace any other members of the family in a conservative substitution.

The terms "polypeptide, peptide, and protein" are used interchangeably herein to refer to a chain of amino acid residues.

An "antigen-binding fragment" of an antibody is a portion of the antibody that is capable of binding to an epitope on an antigen, e.g., the 40 kDa protein, bound by the full antibody.

An "epitope" is a particular region of an antigen, e.g., a protein to which an antibody binds and which is capable of eliciting an immune response.

A "substantially pure" 40 kDa protein is a 40 kDa protein that is at least 60%, by weight, free from the proteins and naturally-occurring organic molecules with which it is naturally associated. Preferably, the preparation is at least 75%, more preferably at least 90%, and most preferably at least 99%, by weight 40 kDa protein. A substantially pure 40 kDa protein can be obtained, for example, by affinity chromatography using antibodies or monoclonal antibodies described herein, and/or by physical purification techniques.

An "isolated" antibody is an antibody which is substantially free from other naturally-occurring organic molecules with which it is naturally associated.

An antibody or other molecule that blocks cell proliferation is an antibody or molecule that inhibits cell cycle, division, or both.

By "homotypic aggregation" is meant a biologically active process whereby cells of the same type are stimulated to adhere to one another.

A "reporter group" is a molecule or compound that has a physical or chemical characteristic such as luminescence, fluorescence, enzymatic activity, electron density, or radioactivity that can be readily measured or detected by appropriate detector systems or procedures.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

The invention features antibodies that recognize a 40 kDa protein which is expressed on tumor cells. The antibodies can be used to inhibit proliferation of tumor cells and induce apoptosis of tumor cells to which they specifically bind. The monoclonal antibodies can be used diagnostically (e.g., to determine the presence of malignant cells), or can be used therapeutically to treat tumor cells by themselves or through their delivery of an attached antitumor agent.

Other features and advantages of the invention will be apparent from the following detailed description, and from the claims.

BRIEF DESCRIPTION OF THE DRAWING

FIGS. 2A-D are four flow cytometric graphs showing the expression of the 40 kDa protein on Day 14 fetal thymus (FIG. 2A), total adult spleen (FIG. 2B), total adult thymus (FIG. 2C) and total adult bone marrow (FIG. 2D) as detected by DMF10.62.3.

FIGS. 3A-G are seven flow cytometric graphs showing the expression of the 40 kDa protein on unstimulated, freshly harvested T and B cells (FIG. 3A), activated T cells at 24 hours (FIG. 3B), activated T cells at 48 hours (FIG. 3C), activated T cells at 72 hours (FIG. 3D), activated splenic B cells at 24 hours (FIG. 3E), activated splenic B cells at 48 hours (FIG. 3F) and activated splenic B cells at 72 hours (FIG. 3G) as detected by DMF10.62.3.

FIGS. 5A-I are nine flow cytometric graphs showing the induction of apoptosis in E710.2.3 cells treated with 1 μg/ml of DMF10.62.3 for 1 hour (FIG. 5A), 1 μg/ml of DMF10.62.3 for 2 hours (FIG. 5B), 1 μg/ml of DMF10.62.3 for 3 hours (FIG. 5C), Hamster IgG for 3 hours (FIG. 5D), 15 μg/ml DMF10.62.3 for 1 hour (FIG. 5E), 15 μg/ml DMF10.62.3 for 2 hours (FIG. 5F), 15 μg/ml DMF10.62.3 for 3 hours (FIG. 5G), Hamster IgG for 3 hours (FIG. 5H), and no antibodies (FIG. 5I).

DETAILED DESCRIPTION

Figure 1A:
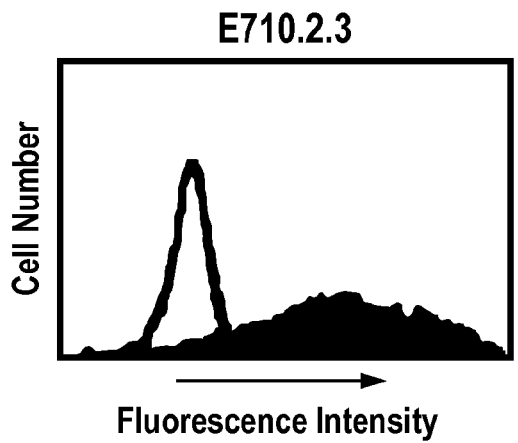
FIGS. 1A-D are four flow cytometric graphs showing the expression of the 40 kDa protein on E710.2.3 (FIG. 1A), A20 (FIG. 1B), Jurkat (FIG. 1C), and RF33.70 (FIG. 1D) as detected by DMF10.62.3.
Figure 1B:
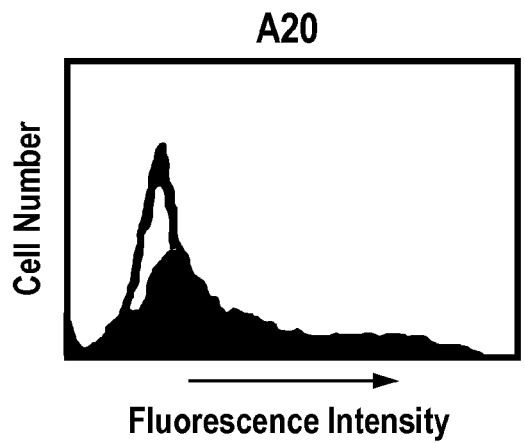
Figure 1C:
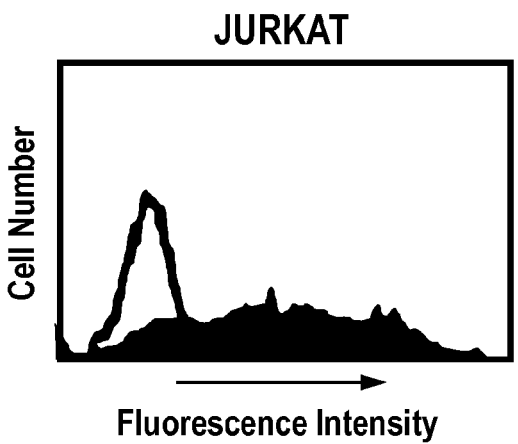

The present invention features antibodies, e.g., monoclonal antibodies, that specifically bind to a 40 kDa protein. The 40 kDa protein is a novel cell surface protein expressed on a variety of types of tumor cells including thymic lymphoma, T-cell tumor, a B-cell lymphoma, melanoma, osteosarcoma, and acute T-cell leukemia and in a variety of different species including humans, monkeys, and mice. The antibodies show no reactivity with normal adult hemopoietic cells. Upon binding of an antibody of the invention to a cell that expresses the 40 kDa protein, the cell stops proliferating and undergoes apoptosis. The 40 kDa protein is a novel death inducing protein based on the observation that that when monoclonal antibodies bind to this protein on a cell, the cells undergo apoptosis.

Three hybridoma cell lines that produce monoclonal antibodies that specifically bind to the 40 kDa protein have been deposited with the ATCC under Accession No. PTA-377 (DMF10.62.3), Accession No. PTA-405 (DMF10.167.4), or Accession No. PTA-404 (DMF10.34.36).

The antibodies described herein have a variety of uses. The antibodies can be used in in vitro diagnostic assays to determine the presence of malignant cells in mammalian, e.g., human, tissues. The antibodies can also be used to localize tumors in vivo by administering to a subject an isolated antibody described herein which is labeled with a reporter group. The antibodies also have therapeutic applications. In addition, the antibodies can be used to treat tumors or deliver an antitumor agent.

Methods of Making Antibodies

Antibodies are immunoglobulin molecules and immunologically active portions of immunoglobulin molecules. Examples of fragments of immunoglobulin molecules include fragments of an antibody, e.g., F(ab) and F(ab')$_2$ portions, which can specifically bind to the 40 kDa protein. Fragments can be generated by treating the antibody with an enzyme such as pepsin. The term monoclonal antibody or monoclonal antibody composition refers to a population of antibody molecules that contain only one species of an antigen binding site capable of immunoreacting with a particular epitope of a polypeptide or protein. A monoclonal antibody composition thus typically displays a single binding affinity for the protein to which it specifically binds Immunization Polyclonal and monoclonal antibodies against the 40 kDa protein can be raised by immunizing a suitable subject (e.g., a rabbit, goat, mouse or other mammal) with an immunogenic preparation which contains a suitable immunogen. Immunogens include cells such as cells from immortalized cell lines E710.2.3, RMA-S, CTLL, LB 117.4, A20, WEHI-231, PBK101A2, C2.3, B16, MC57, WOP-3027, 293T, 143Btk, Jurkat, or Cos, which have all been shown to express the novel 40 kDa protein.

Alternatively, the immunogen can be the purified or isolated 40 kDa protein itself For example, the monoclonal antibody produced by the hybridoma cell line deposited as ATCC No. PTA-377, PTA-405, or PTA-404 can be used to isolate the protein from a cell which produces the protein, e.g., E710.2.3, RMA-S, CTLL, LB17.4, A20, WEHI-231, PBK101A2, C2.3, B16, MC57, WOP-3027, 293T, 143Btk, Jurkat, or Cos, using affinity chromatography, immunoprecipitation or other techniques which are well known in the art.

The antibodies raised in the subject can then be screened to determine if the antibodies bind to fetal thymocytes while not binding to adult thymocytes. Such antibodies can be further screened in the assays described herein. For example, these antibodies can be assayed to determine if they inhibit cell proliferation of cells to which they bind; induce homotypic aggregation of cells; and/or induce apoptosis in cells to which they bind. Suitable methods to identify an antibody with the desired characteristics are described herein. For example, the ability of an antibody to induce cell death upon binding to a cell can be assayed using commercially available kits from R&D (Minneapolis, Minn.) or Pharmingen (San Diego, Calif.).

The unit dose of immunogen (e.g., the purified protein, tumor cell expressing the protein, or recombinantly expressed 40 kDa protein) and the immunization regimen will depend upon the subject to be immunized, its immune status, and the body weight of the subject. To enhance an immune response in the subject, an immunogen can be administered with an adjuvant, such as Freund's complete or incomplete adjuvant.

Immunization of a subject with an immunogen as described above induces a polyclonal antibody response. The antibody titer in the immunized subject can be monitored over time by standard techniques such as an ELISA using an immobilized antigen, e.g., the 40 kDa protein described herein.

Other methods of raising antibodies against the 40 kDa protein include using transgenic mice which express human immunoglobin genes (see, e.g., Wood et al. PCT publication WO 91/00906, Kucherlapati et al. PCT publication WO 91/10741; or Lonberg et al. PCT publication WO 92/03918). Alternatively, human monoclonal antibodies can be produced by introducing an antigen into immune deficient mice that have been engrafted with human antibody-producing cells or tissues (e.g., human bone marrow cells, peripheral blood lymphocytes (PBL), human fetal lymph node tissue, or hematopoietic stem cells). Such methods include raising antibodies in SCID-hu mice (see Duchosal et al. PCT publication WO 93/05796; U.S. Pat. No. 5,411,749; or McCune et al. (1988) *Science* 241:1632-1639)) or Rag-1/Rag-2 deficient mice. Human antibody-immune deficient mice are also commercially available. For example, Rag-2 deficient mice are available from Taconic Farms (Germantown, N.Y.).

Hybridomas

Monoclonal antibodies can be generated by immunizing a subject with an immunogen. At the appropriate time after immunization, e.g., when the antibody titers are at a sufficiently high level, antibody producing cells can be harvested from an immunized animal and used to prepare monoclonal antibodies using standard techniques. For example, the antibody producing cells can be fused by standard somatic cell fusion procedures with immortalizing cells such as myeloma cells to yield hybridoma cells. Such techniques are well known in the art, and include, for example, the hybridoma technique as originally developed by Kohler and Milstein, (1975) *Nature,* 256: 495497), the human B cell hybridoma technique (Kozbar et al., (1983) *Immunology Today,* 4: 72), and the EBV-hybridoma technique to produce human monoclonal antibodies (Cole et al., (1985) *Monoclonal Antibodies and Cancer Therapy,* Alan R. Liss, Inc. pp. 77-96). The technology for producing monoclonal antibody hybridomas is well known.

Monoclonal antibodies can also be made by havesting antibody producing cells, e.g., splenocytes, from transgenic mice expressing human immunogloulin genes and which have been immunized with the 40 kDa protein. The splenocytes can be immortalized through fusion with human myelomas or through transformation with Epstein-Barr virus (EBV). These hybridomas can be made using human B cell- or EBV-hybridoma techniques described in the art (see, e.g., Boyle et al., European Patent Publication No. 0 614 984).

Hybridoma cells producing a monoclonal antibody which specifically binds to the 40 kDa protein are detected by screening the hybridoma culture supernatants by, for example, screening to select antibodies that specifically bind to the immobilized 40 kDa protein, or by testing the antibodies as described herein to determine if the antibodies have the desired characteristics, e.g., the ability to inhibit cell proliferation.

Hybridoma cells that produce monoclonal antibodies that test positive in the screening assays described herein can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (see, e.g., R. H. Kenneth, in *Monoclonal Antibodies: A New Dimension In Biological Analyses*, Plenum Publishing Corp., New York, N.Y. (1980). Conditioned hybridoma culture supernatant containing the antibody can then be collected.

Recombinant Combinatorial Antibody Libraries

Monoclonal antibodies can be engineered by constructing a recombinant combinatorial immunoglobulin library and screening the library with the 40 kDa protein. Kits for generating and screening phage display libraries are commercially available (e.g., the Pharmacia *Recombinant Phage Antibody System*, Catalog No. 27-9400-01; and the Stratagene *SurfZAP Phage Display Kit,* Catalog No. 240612). Briefly, the antibody library is screened to identify and isolate phages that express an antibody that specifically binds to the 40 kDa protein. In a preferred embodiment, the primary screening of the library involves screening with an immobilized 40 kDa protein.

Following screening, the display phage is isolated and the nucleic acid encoding the selected antibody can be recovered from the display phage (e.g., from the phage genome) and subcloned into other expression vectors by well known recombinant DNA techniques. The nucleic acid can be further manipulated (e.g., linked to nucleic acid encoding additional immunoglobulin domains, such as additional constant regions) and/or expressed in a host cell.

Chimeric and Humanized Antibodies

Recombinant forms of antibodies, such as chimeric and humanized antibodies, can also be prepared to minimize the response by a human patient to the antibody. When antibodies produced in non-human subjects or derived from expression of non-human antibody genes are used therapeutically in humans, they are recognized to varying degrees as foreign, and an immune response may be generated in the patient. One approach to minimize or eliminate this immune reaction is to produce chimeric antibody derivatives, i.e., antibody molecules that combine a non-human animal variable region and a human constant region. Such antibodies retain the epitope binding specificity of the original monoclonal antibody, but may be less immunogenic when administered to humans, and therefore more likely to be tolerated by the patient.

Chimeric monoclonal antibodies can be produced by recombinant DNA techniques known in the art. For example, a gene encoding the constant region of a non-human antibody molecule is substituted with a gene encoding a human constant region (see Robinson et al., PCT Patent Publication PCT/US86/02269; Akira, et al., European Patent Application 184,187; or Taniguchi, M., European Patent Application 171, 496).

A chimeric antibody can be further "humanized" by replacing portions of the variable region not involved in antigen binding with equivalent portions from human variable regions. General reviews of "humanized" chimeric antibodies are provided by Morrison, S. L. (1985) Science, 229:1202-1207 and by Oi et al: (1986) *BioTechniques,* 4-214. Such methods include isolating, manipulating, and expressing the nucleic acid sequences that encode all or part of an immunoglobulin variable region from at least one of a heavy or light chain. The cDNA encoding the humanized chimeric antibody, or fragment thereof, can then be cloned into an appropriate expression vector. Suitable "humanized" antibodies can be alternatively produced by (complementarity determining region (CDR) substitution (see U.S. Pat. No. 5,225,539; Jones et al. (1986) *Nature* 321:552-525; Verhoeyan et al. (1988) *Science* 239:1.534; and Beidler et al. (1988) *J. Immunol.* 141:4053-4060).

Epitope imprinting can also be used to produce a "human" antibody polypeptide dimer that retains the binding specificity of the hamster antibodies specific for the 40 kDa protein produced by the hybridoma deposited as ATCC No. PTA-377, ATCC No. PTA-405, or ATCC No. PTA-404. Briefly, a gene encoding a non-human variable region (VH) with specific binding to an antigen and a human constant region (CH1), is expressed in E. coli and infected with a phage library of human VλCλ genes. Phage displaying antibody fragments are then screened for binding to the 40 kDa protein. Selected human VX genes are recloned for expression of VλCλ chains and E. coli harboring these chains are infected with a phage library of human VHCH1 genes and the library is subject to rounds of screening with antigen coated tubes. See Hoogenboom et al. PCT publication WO 93/06213.

Antibody Fragments

The present invention encompasses new antitumor antibodies and any fragments thereof containing the active binding region of the antibody, such as Fab, F(ab')2, and Fv fragments. Such fragments can be produced from the antibody using techniques well established in the art (see, e.g., Rousseaux et al., in Methods Enzymol., 121:663-69 Academic Press, (1986)). For example, the $F(ab')_2$ fragments can be produced by pepsin digestion of the antibody molecule, and the Fab fragments can be generated by reducing the disulphide bridges of the $F(ab')_2$ fragments.

Utility of Antibodies

The antibodies described herein have a variety of uses. The antibodies can be used in vitro for diagnostic purposes to determine the presence of malignant cells in human tissues. The method involves examining a tissue sample for the presence of the 40 kDa protein. For example, the tissue sample can be contacted with the monoclonal antibody produced by the hybridoma cell line ATCC NO: PTA-377, ATCC No. PTA-405, or ATCC No. PTA-404, and the ability of the antibody to specifically bind to the cells in the tissue sample is determined. Binding indicates the presence of a tumor cell. Alternatively, the antibody can also be used to screen blood samples for released antigen.

The antibodies can also be used to localize a tumor in vivo by administering to a subject an isolated antibody of the present invention which is labeled with a reporter group which gives a detectable signal. The bound antibodies are then detected using external scintigraphy, emission tomography, or radionuclear scanning. The method can be used to stage a cancer in a patient with respect to the extent of the disease and to monitor changes in response to therapy.

The antibodies also have therapeutic applications. The new antibodies can be used to treat tumors, because specific binding of the antibody to the tumor cell causes the cell to stop proliferating and to die.

The antibodies can also be used therapeutically, e.g., as targeting agents, to deliver antitumor agents to the tumors. Such anti-tumor agents include chemotherapeutic drugs, toxins, immunological response modulators, enzymes, and radioisotopes.

Detectable Labels

The antibodies that react with the 40 kDa protein can be used diagnostically, e.g., to detect the presence of a tumor in a subject. Detection can be facilitated by coupling the antibody to a detectable label. Examples of detectable labels include various enzymes, prosthetic groups, fluorescent materials, luminescent materials, bioluminescent materials, electron dense labels, labels for MRI, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoeryhrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies as Targeting Agents

The antibodies and antibody fragments described herein can be conjugated to a moiety and the antibody can be used to direct the moiety to the site of a tumor cell which expresses the 40 kDa protein. Examples of moieties include, toxins, radionuclides, or chemotherapeutic agents which can be used to kill tumor cells, or imaging agents which can be used to locate and size tumors expressing the 40 kDa protein. The antibodies used to direct the moiety to the tumor in humans are preferably monoclonal antibodies, e.g., a humanized monoclonal antibodies.

The antibody can be fused to the moiety, e.g., the toxin, either by virtue of the moiety and the antibody being encoded by a fused gene which encodes a hybrid protein molecule, or by means of conjugation, e.g., a non-peptide covalent bond, e.g., a non-amide bond, which is used to join separately produced antibody and the moiety.

The antibody described herein can also be fused to another antibody that is specific for immune cells and stimulates the immune cells to kill the tumor.

Toxins

Useful toxin molecules include peptide toxins, which are significantly cytotoxic when present intracellularly. Examples of toxins include cytotoxins, metabolic disrupters (inhibitors and activators) that disrupt enzymatic activity and thereby kill tumor cells, and radioactive molecules that kill all cells within a defined radius of the effector portion. A metabolic disrupter is a molecule, e.g., an enzyme or a cytokine, that changes the metabolism of a cell such that its normal function is altered. Broadly, the term toxin includes any effector that causes death to a tumor cell.

Many peptide toxins have a generalized eukaryotic receptor binding domain; in these instances the toxin must be modified to prevent killing cells not bearing the targeted protein (e.g., to prevent killing of cells not bearing the 40 kDa protein but having a receptor for the unmodified toxin). Such modifications must be made in a manner that preserves the cytotoxic function of the molecule. Potentially useful toxins include, but are not limited to: diphtheria toxin, cholera toxin, ricin, O-Shiga-like toxin (SLT-I, SLT-II, $SLT\text{-}II_v$), LT toxin, C3 toxin, Shiga toxin, pertussis toxin, tetanus toxin, *Pseudomonas* exotoxin, alorin, saponin, modeccin, and gelanin. Other toxins include tumor necrosis factor alpha (TNF-a) and lymphotoxin (LT). Another toxin which has antitumor activity is calicheamicin gamma 1, a diyne-ene containing antitumor antibiotic with considerable potency against tumors (Zein, N., et al., *Science,* 240:1198-201 (1988)).

As an example, diphtheria toxin can be conjugated to the antibodies described herein. Diphtheria toxin, whose sequence is known, is described in detail in Murphy, U.S. Pat. No. 4,675,382, which is incorporated herein by reference. The natural diphtheria toxin molecule secreted by *Corynebacterium diphtheriae* consists of several functional domains that can be characterized, starting at the amino terminal end of the molecule, as enzymatically-active Fragment A (amino acids $Gly_1$-$Arg_{193}$) and Fragment B (amino acids $Ser_{194}$-$Ser_{535}$), which includes a translocation domain and a generalized cell binding domain (amino acid residues 475 through 535).

Linkage of Toxins to Antibodies

The antibody and the toxin moiety can be linked in any of several ways. If the compound is produced by expression of a fused gene, a peptide bond serves as the link between the cytotoxin and the antibody. Alternatively, the toxin and the antibody can be produced separately and later coupled by means of a non-peptide covalent bond. For example, the covalent linkage may take the form of a disulfide bond. In this case, the DNA encoding this antibody can be engineered, by conventional methods, to contain an extra cysteine codon.

For a disulfide bond linkage, the toxin molecule is also derivatized with a sulfhydryl is group reactive with the cysteine of the modified antibody. In the case of a peptide toxin this linkage can be accomplished by inserting a cysteine codon into the DNA sequence encoding the toxin. Alternatively, a sulfhydryl group, either by itself or as part of a cysteine residue, can be introduced using solid phase polypeptide techniques. For example, the introduction of sulfhydryl groups into peptides is described by Hiskey, *Peptides*, 3:137 (1981).

Derivatization can also be carried out according to the method described for the derivatization of a peptide hormone in Bacha et al., U.S. Pat. No. 4,468,382. The introduction of sulfhydryl groups into proteins is described in Maasen et al., *Eur. J. Biochem.*, 134:32 (1983). Once the required sulfhydryl groups are present, the cytotoxin and the antibody are purified, both sulfur groups are reduced, cytotoxin and antibody are mixed (in a ratio of about 1:5 to 1:20), and disulfide bond formation is allowed to proceed to completion (generally 20 to 30 minutes) at room temperature. The mixture is then dialyzed against phosphate buffered saline to remove unreacted antibody and toxin molecules. Sephadex$^R$ chromatography or the like is used to separate the desired toxin-antibody conjugate compounds from toxin-toxin and antibody-antibody conjugates on the basis of size Immune Response Modulators The antitumor moiety can also be a modulator of the immune system that either activates or inhibits the body's immune system at the local level. For example, cytokines, e.g., lymphokines such as IL-2, delivered to a tumor can cause the proliferation of cytotoxic T-lymphocytes or natural killer cells in the vicinity of the tumor Radioactive Molecules The moiety or reporter group can also be a radioactive molecule, e.g., a radionucleotide, or a so-called sensitizer, e.g., a precursor molecule, that becomes radioactive under specific conditions, e.g., boron when exposed to a beam of low-energy neutrons, in the so-called "boron neutron capture therapy" (BNCT). Barth et al., *Scientific American*, October 1990:100-107 (1990). Compounds with such radioactive effector portions can be used both to inhibit tumor cell proliferation and to label the tumor cells for imaging purposes.

Radionuclides are single atom radioactive molecules that can emit either α, β, or γ particles. Alpha particle emitters are preferred to β or γ particle emitters, because they release far higher energy emissions over a shorter distance, and are therefore efficient without significantly penetrating, and harming, normal tissues. Suitable a particle emitting radionuclides include $^{211}$At, $^{212}$Pb, and $^{212}$Bi.

The radioactive molecule must be tightly linked to the antibody either directly or by a bifunctional chelate. This chelate must not allow elution and thus premature release of the radioactive molecule in vivo. Waldmann, *Science*, 252: 1657-62 (1991).

To adapt BNCT to the present invention, a stable isotope of boron, e.g., boron 10, is selected as the antitumor moiety or effector portion of the compound. The boron is delivered to and concentrates in or on the tumor cells by the specific binding of the antibody to the tumor cell. After a time that allows a sufficient amount of the boron to accumulate, the tumor is imaged and irradiated with a beam of low-energy neutrons, having an energy of about 0.025 eV. While this neutron irradiation, by itself, causes little damage to either the healthy tissue surrounding the tumor, or the tumor itself, boron 10 (e.g., on the surface of a tumor cell) captures the neutrons, thereby forming an unstable isotope, boron 11. Boron 11 instantly fissions yielding lithium 7 nuclei and energetic a particles, about 2.79 million Ev. These heavy particles are a highly lethal, but very localized, form of radiation, because particles have a path length of only about one cell diameter (10 microns).

Calculations have shown that to destroy a tumor cell, about one billion boron atoms are required along with a flow of thermal neutrons of from $10^{12}$ to $10^{13}$ neutrons per square centimeter, so that the radiation generated by the a particles exceeds the background radiation generated by neutron capture reactions with nitrogen and hydrogen.

Imaging Moieties

The antibodies described herein specifically bind to the 40 kDa protein and are thus also useful to detect human tumors. One such approach involves the detection of tumors in vivo by tumor imaging techniques using the antibody labeled with an appropriate moiety or reporter group, e.g., an imaging reagent that produces a detectable signal. Imaging reagents and procedures for labeling antibodies with such reagents are well known (see, e.g., Wensel and Meares, Radio Immunoimaging and Radioimmunotherapy, Elsevier, New York (1983); Colcher et al., Meth. Enzymol., 121:802-16 (1986)). The labeled antibody can be detected by a technique such as radionuclear scanning (see, e.g., Bradwell et al. in Monoclonal Antibodies for Cancer Detection and Therapy, Baldwin et al. (eds.), pp. 65-85, Academic Press (1985)).

Administration

The antibodies described herein can be administered to a subject, e.g., an animal or a human, to image or treat tumors. The antibodies can be administered alone, or in a mixture, e.g., in the presence of a pharmaceutically acceptable excipient or carrier (e.g., physiological saline). The excipient or carrier is selected on the basis of the mode and route of administration. Suitable pharmaceutical carriers are described in *Remington's Pharmaceutical Sciences* (E. W. Martin), a well known reference text in this field, and in the USP/NF (United States Pharmacopeia and the National Formularly).

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

The most effective mode of administration and dosage regimen for the compositions of this invention depend upon the severity and course of the disease, the patient's health and response to treatment, and the judgment of the treating physician. Accordingly, the dosages of the compositions should be titrated to the individual patient. An effective dose of the antibody compositions of this invention is in the range of from about 1 ug to about 5000 mg, preferably about 1 to about 500 mg, or preferably about 100-200 mg.

Diagnostic Kits

The invention also encompasses diagnostic kits for carrying out the methods disclosed above. The diagnostic kit includes (a) a monoclonal antibody described herein, and (b) a conjugate of a specific binding partner for the antibody and a label for detecting bound antibody. The kit may also include ancillary agents such as buffering agents and protein stabilizing agents, e.g., polysaccharides and the like. The diagnostic kit may further include, where necessary, other components of a signal-producing system including agents for reducing background interference, control reagents, and an apparatus for conducting a test. In another embodiment, the diagnostic kit includes a conjugate of a monoclonal antibody of the invention and a label capable of producing a detectable signal. Ancillary agents as mentioned above may also be present. Instructions on how to use the diagnostic kit are generally also included.

Polypeptides

The monoclonal antibodies described herein can be used to isolate and characterize the 40 kDa protein to which they bind. The protein recognized by the monoclonal antibody is a novel cell surface protein found on a variety of tumor cells including thymic lymphoma, T-cell tumor, a B-cell lymphoma, melanoma, osteosarcoma, and acute T-cell leukemia. The protein is a death inducing molecule based on the observation that when monoclonal antibodies bind to this protein, the cell on which the protein is expressed dies.

The protein recognized by the monoclonal antibodies of the invention can be isolated from cells expressing the protein (e.g., E710.2.3, RMA-S, CTLL, LB17.4, A20, WEHI-23 1, PBK101A2, C2.3, B16, MC57, WOP-3027, 293T, 143Btk, Jurkat, or Cos). For example, the monoclonal antibodies described herein can be used to immunoprecipitate the protein. To determine the sequence of the protein, the protein can be purified by SDS-PAGE, electroblotted onto an Immobilon membrane (Millipore Corp., Bedford, Mass.), and the membrane stained with Coomassie Brilliant Blue. The stained protein band (Mr=40 kDa) can then be excised with a razor blade for subsequent amino-terminal sequence analysis. Amino-terminal sequence analysis, such as automated Edman degradation, are well known in the art.

The invention also features fusion proteins that include the 40 kDa protein fused to an unrelated protein. The unrelated protein can be selected to facilitate purification, detection, solubilization, or to provide some other function. Fusion proteins can be produced synthetically, or the protein can be linked to an unrelated protein using an appropriate coupling reagent, e.g., dicyclohexylcarbodiimide (DCC). Alternatively, fusion proteins can be produced recombinately by cloning a nucleotide sequence which expresses the fusion protein into an appropriate expression vector. The recombinant fusion polypeptide can then be purified from the culture medium or from lysates of the cells.

The 40 kDa protein is useful, e.g., as a vaccine to immunize against certain tumors. Procedures for preparing such vaccines are known in the art (see, e.g., Estin et al., Proc. Nat'l. Acad. Sci. (USA), 85:1052 (1988)). Briefly, recombinant viruses are constructed for expression of the cloned tumor-associated protein. Cells infected with the recombinant viruses will express the protein at the surface of the cells together with the host's histocompatibility antigens and immunogenic viral proteins. This favors the induction of cellular immunity which plays a key role in tumor rejection.

The invention also provides a method for identifying modulators, i.e., test compounds or agents (e.g., peptides, peptidomimetics, small molecules or drugs) which bind to the 40 kDa protein or which have a stimulatory or inhibitory effect on expression or activity of the 40 kDa protein. For example, an antagonist of the 40 kDa protein would be useful for inhibiting apoptosis in a cell. This antagonist might play a role in inhibiting abherant apoptosis in a subject.

EXAMPLES

Example 1

Generation of Antitumor Antibodies

In an attempt to identify novel functional molecules that may be involved in the growth or survival of lymphomas and/or in normal thymocyte function, hybridomas from hamsters injected with E710.2.3 were generated as follows. Armenian hamsters were injected intraperitoneally with 10 million E710.2.3 and boosted 7-10 times before fusion. Fusions were performed using the fusion partner P3X63-AG8.653 as described (Schreiber et al. (1985) *Immunol* 134: 1609). Supernatants from hybrids were first screened using immunofluorescence and flow cytometry for the ability to bind to E710.2.3A. One particular antibody, referred to herein as DMF10.62.3, stained the surface of E710.2.3 brightly.

Figure 1D:
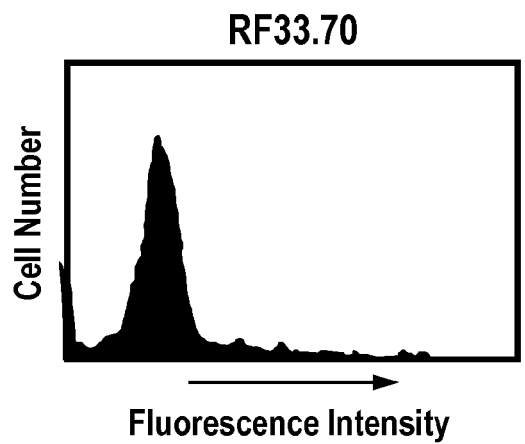

Immunofluorescence analysis revealed that DMF10.62.3 reacted with a number of murine cell lines (Table I), but was absent from others (Table II). Positive cell lines included some T cell lines (e.g. RMA-S), several B cell lymphomas (e.g. A20 and WEHI-231), and a macrophage cell line (C2.3). DMF10.62.3 also specifically bound to several immortalized cells of non-hematopoietic origin, inducing a stromal cell line (PBK101A2), a melanoma (B16), a sarcoma (MC57), and a polyoma-transformed fibroblast (WOP-3027). Several other immature (e.g., G58.2) and mature T cells (e.g., EL4), a macrophage (e.g., A3.1), a dendritic cell (DC2.4), and a fibroblast cell line (LADp31) were negative for DMF10.62.3. Interestingly, the mAb also reacted with several human immortalized cell lines, including Jurkat, 293T and 143Btk- and also with a monkey SV40-transformed kidney cell line, Cos7. DMF10.62.3 did not bind to certain human cell lines, such as the B lymphoblastoid cell, 721, and the cervical carcinoma cell HeLa. Staining patterns of representative cell lines are shown in FIG. 1 for the DMF10.62.3-positive cells E710.2.3 (FIG. 1A), A20 (FIG. 1B) and Jurkat (FIG. 1C) and the DMF10.62.3-negative cell, RF33.70 (FIG. 1D).

TABLE I

| CELL LINE | DESCRIPTION |
|---|---|
| E710.2.3 | Murine thymic lymphoma |
| RMA-S | Murine T cell tumor |
| CTLL | Murine IL-2 dependent T cell line |
| LB27.4 | Murine B cell hybridoma |
| A20 | Murine B cell lymphoma |
| WEHI-231 | Murine B cell lymphoma |
| PBK101A2 | Murine thymic stromal cell line |
| C2.3 | Murine immortalized bone marrow macrophage |
| B16 | Murine melanoma |
| MC57 | Murine methylcholanthrene-induced tumor |
| WOP-3027 | Murine polyoma-transformed fibroblast |
| 293T | Human transformed primary embryonal kidney |
| 143Btk- | Human osteosarcoma |

The above data indicated that new antibodies specifically bind to many but not all immortalized cell lines, and that binding is not species or cell lineage-restricted.

TABLE II

| CELL LINE | DESCRIPTION |
|---|---|
| RF33.70 | Murine T-T hybrid |
| DO11.10 | Murine T-T hybrid |
| 13G7.3.2 | Murine T-T hybrid |
| HT-2 | Murine IL-2 dependent T cell line |
| EL-4 | Murine T cell lymphoma |
| G58.2 | Murine thymic lymphoma |
| NFC105 | Murine thymic lymphoma |
| P815 | Murine mastocytoma |
| P388D1 | Murine monocyte/macrophage tumor |
| $LAD_p31$ | Mouse L cell line |
| A3.1 | Murine immortalized bone marrow-derived macrophage |
| DC2.4 | Murine immortalized dendritic cell line |
| 721 | Human B cell line |
| HeLa | Human epithelial cervical carcinoma |
| E36 | Hamster lung carcinoma |
| BHK-21 | Hamster kidney cell line |
| CHO | Chinese hamster ovary |

Example 2

Expression of the Molecule Recognized by DMF10.62.3

Expression of the molecule recognized by DMF10.62.3 was examined in fetal thymocytes as follows. Timed pregnancies of C57BI/10 mice produced embryos that were sacrificed at fetal day 14. The fetal thymi were harvested in PBS using an Eppendorf tube glass plunger. Single cell suspensions were incubated for 20 minutes on ice with an anti-Fc gamma receptor II/III (Pharmingen) to block Fc receptors. Cells were subsequently stained with either DMF10.62.3 or hamster IgG for 30 minutes followed by FITC conjugated goat anti-hamster, along with allophycoyanin (APC)-conjugated anti-Thy 1.2 (Pharmingen). In some experiments, anti-CD25 conjugated to PE and anti-CD44 conjugated to Cy-Chrome (Pharmingen) were also included. The stained cells were fixed overnight in 1% paraformaldehyde and subsequently analyzed by flow cytometry.

Results showed that day 14 fetal thymocytes stained with DMF10.62.3 were positive for the 40 kDa protein and the protein was found to be present on Thy 1.2 positive cells (FIG. 2A). Interestingly, the protein was present on both $CD25^+$ $CD44^+$ fetal thymocytes as well as $CD44^+CD25^-$ fetal thymocytes. However, staining of adult thymus (FIG. 2C), adult spleen (FIG. 2B). and adult bone marrow cells (FIG. 2D) showed that the protein recognized by DMF10.62.3 is not present on any of these cells at levels above those seen with control hamster IgG. Furthermore, the protein could not be detected on adult $CD4^-CD8^-$ thymocytes after gating on $CD4^-CD8^-$ cells in a multiparameter analysis, by flow cytometry or analysis of this population from RAG−/−mice. Day 14 fetal liver cells were also non-reactive with DMF10.62.3.

To determine if the protein recognized by DMF10.62.3 was present on normal, activated cells, splenic T cells were activated with the T cell mitogen ConA and stained for expression of the protein recognized by DMF10.62.3 as follows. Spleen, thymus, and bone marrow cells were prepared from adult (4-6 months old) Balb/c or C57B1/6 mice. Red blood corpuscles were removed from spleen cells suspensions using tris ammonium chloride lysis. Unstimulated cells were stained immediately. Lymphoblasts were stimulated in culture with 1 μg/ml of ConA or 10 μg/ml of LPS. After 1-3 days of culture, cells were stained for the expression of DMF10.62.3. No significant staining above background was seen in unstimulated cells (FIG. 3A) or cells stimulated with ConA at 24 (FIG. 3B), 48. (FIG. 3C), or 72 (FIG. 3D) hours after activation (no shift in FACs profile). As a positive control, ConA stimulated cells were stained with CD25. As expected, ConA treatment resulted in a significant increase in expression of CD25 on these cells as compared to unstimulated cells (binding of CD25 to cells causes shift of FAC's profile). Similarly, when splenic B cells were activated with lipopolysaccaride (LPS), no staining with DMF10.62.3 was seen at 24 (FIG. 3E), 48 (FIG. 3F), and 72 (FIG. 3G) hours (no shift in FAC's profile), whereas these cells did express CD25 (shift in FAC's profile). The protein recognized by DMF10.62.3 is not present on adult bone marrow cells (FIG. 2D). These data indicate that the protein recognized by DMF10.62.3 is present on some fetal thymocytes, but not on normal quiescent or activated cells of hematopoietic origin in adult animals.

Example 3

DMF10.62.3 Inhibits Proliferation of Tumor Cells

Figure 4A:
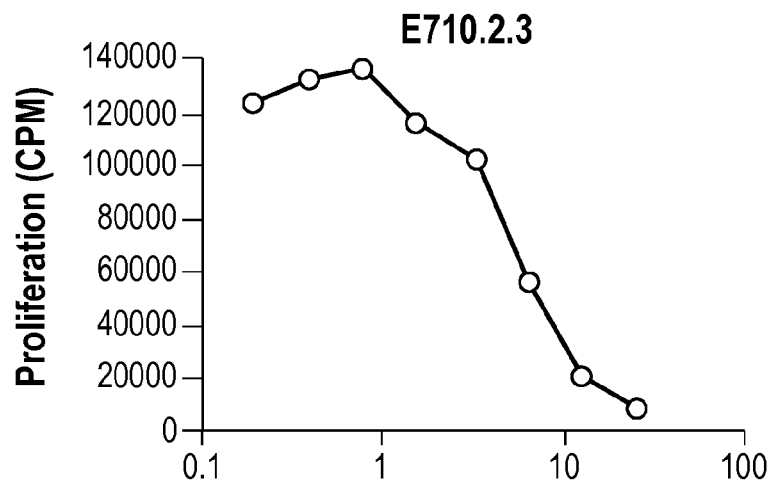
FIGS. 4A-C are three line graphs showing the inhibition of spontaneous proliferation of E710.2.3 cells (FIG. 4A), RMA-S cells (FIG. 4B) or RF33.70 cells (FIG. 4C), by the monoclonal antibody DMF10.62.3.

When grown at low density, and maintained in the absence of PMA, E170.2.3 cells proliferate slowly or not at all. However they proliferate when cocultured with thymocytes. DMF10.62.3 was initially identified by its ability to block this thymocyte-induced proliferation. As shown in Table III, DMF10.62.3 completely inhibits this response (FIG. 4A). Proliferation assays were conducted as follows. E10.2.3 cells were washed free of PMA and cultured in complete RPMI for 48 hours at low cell density ($<10^5$/ml), to reduce background proliferation. Subsequently, $5\times10^3$ cells were cultured for 72 hours in flat bottom microtiter plates with 25 ng/ml PMA or $5\times10^5$ thymocytes in the presence or absence of antibodies. In experiments examining the effects of antibodies on the spontaneous proliferation of cells, E710.2.3 (grown at high density$>10^5$/ml) or RMA-S cells were cultured for 36 hours in the presence or absence of different concentrations of antibody. $^3$H-thymidine (1 TCi/well) was added for the last 5 hours and the incorporation of label into DNA was measured in a J-scintillation counter (Wallac, Gaithersburg, Md.).

TABLE III

|  | Medium | Thymocytes | PMA |
|---|---|---|---|
| Control (no antibody) | 8,699 | 33,802 5 | 4,271 |
| DMF10.62.3 | 938 | 750 | 450 |
| DMF10.132 | 6,646 | 27,156 | 25,216 |

The ability of DMF10.62.3 to inhibit the response of E710.2.3 to other stimuli was also investigated. As shown in Table III, the antibody also blocked PMA-induced proliferation of E710.2.3. Moreover, E710.2.3 spontaneously proliferated when grown at high density, and DMF10.62.3 inhibited this response (FIG. 4A). Proliferation is significantly inhibited at 3 μg/ml and complete inhibition is observed at 12.5 μg/ml. In contrast, hamster IgG had no effect on the response of E710.2.3 (FIG. 4A) to any of these stimuli. Similarly, many of the mAbs from the original fusion bound to E710.2.3, but did not inhibit its proliferation (e.g. DMF10.132) (Table III). Therefore, DMF10.62.3 specifically inhibited the proliferation of E710.2.3 regardless of the stimulus used to induce proliferation.

Figure 4B:
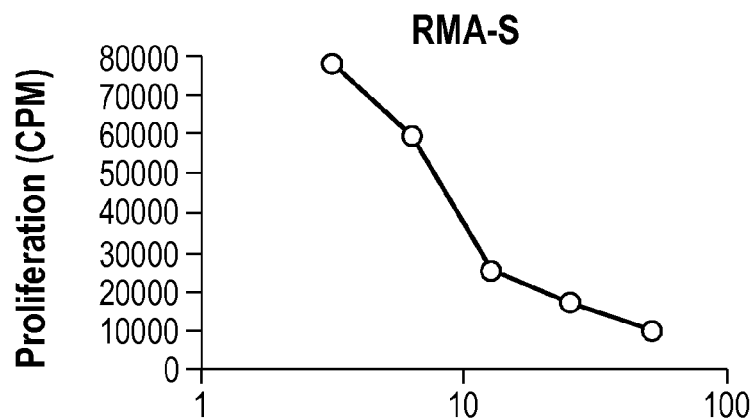
Figure 4C:
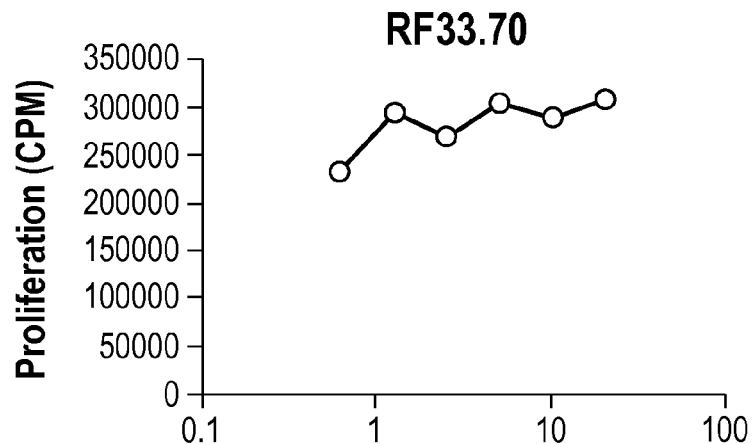

The protein recognized by DMF10.623 is present on a number of other cell lines. Therefore it was of interest to determine if the antibody had a similar effect on their spontaneous proliferation. DMF10.62.3 inhibited the proliferation of RMA-S (FIG. 4B), as well as a number of other cell lines tested. In contrast, the antibody had no effect on the spontaneous proliferation of RF33.70, which was negative for the presence of the DMF10.62.3 protein (FIG. 4C).

Example 4

DMF10.62.3 Induces Cell Death by Apoptosis

Apoptosis was assayed using kits from R&D (Minneapolis, Minn.) and Pharmingen (San Diego, Calif.). Briefly, $2 \times 10^5$ cells were incubated with various concentrations of antibody in 200 it medium. At the end of the incubation, cells were washed 2× in PBS, treated with PI and FITC annexin for 15 minutes, and then analyzed by flow cytometry. DNA fragmentation was assessed by agarose gel electrophoresis on 2% agarose gels as described by Schattner et al. ((1995) *J. Exp. Med.* 182:1557).

Cultures of cells treated with antibody DMF10.62.3 were visually inspected and the number of intact cells was noted to decrease. In addition, the cells no longer excluded the vital dye trypan blue. This observation, as well as the inhibition of proliferation, suggested that the antibody was cytotoxic to the cells. Therefore, studies were performed to determine the mechanism by which DMF10.62.3 was inducing cell death.

Cells can die by apoptosis or necrosis. One of the early changes seen in cells undergoing apoptosis is the externalization of phosphatidylserine on the plasma membrane, and this can be detected by staining with FITC-annexin. Early in the process, the apoptotic cells can exclude vital dyes, such as propidium iodide, and therefore can be identified as FITC-annexin positive and PI-negative. Later in the apoptotic process, membrane integrity is lost and the FITC-annexin positive cells become PI-positive. In contrast, during necrosis cells lose membrane integrity and become simultaneously PI-positive and FITC-annexin positive, without a FITC annexin positive and PI-negative stage.

In the FACs profiles of FIG. 5A to 5I, cells in the left lower quadrant are live cells, cells in the lower right quadrant are undergoing apoptosis (FITC-annexin positive), and cells in the upper right quadrant are cells that are dead by apoptosis and/or necrosis (PI-positive and FITC-annexin positive). The percentage of cells in each quadrant is also shown. In the present study, a percentage of E710.2.3 cells underwent spontaneous apoptosis in culture (10.9 to 15% Annexin+, PI–). However, as little as 1 μg/ml of DMF10.62.3 caused a significant increase in apoptosis in 1 hour (28.9% Annexin+, PI–; FIG. 5A), and this apoptosis increased over time (48.6% Annexin+, PI– positive by 3 hours) (FIG. 5C). Higher amounts of DMF10.62.3 (15 μg/ml)-stimulated apoptosis more quickly in time (37.1% Annexin+, PI– positive by 1 hour) and in more cells (FIG. 5E-G). In contrast, treatment with similar amounts of hamster IgG had no significant effect above that of medium alone (FIGS. 5D, 5H, 5I). Apoptosis was also verified by visualizing DNA fragmentation by agarose gel electrophoresis.

Since the protein recognized by DMF10.62.3 was expressed on other cells, and this antibody inhibited their proliferation (where tested), it was further investigated whether DMF10.62.3 also stimulated them to undergo apoptosis. DMF10.62.3 caused significant apoptosis of the murine cells lines RMA-S, CTLL, LB27.4 and A20 and the human cell lines Jurkat and 143BTK-(Table IV). Apoptosis was induced using 15 μg/ml of DMF10.62.3 and increased with higher concentrations of antibody. In contrast, DMF10.62.3 did not cause apoptosis in RF33.70, which is negative for the protein. The level of apoptosis induced by DMF10.62.3 varied among different cell lines and appears to be dependent on the level of surface expression as well the percentage of cells within the population expressing the protein (Table IV). For example, most E710.2.3 and RMA cells, expressed the protein at high levels and DMF10.62.3 induced high levels of apoptosis in both of these cell lines. In contrast, few A20 and LB27.4 cells expressed the 40 kDa protein at lower levels and DMF10.62.3 induced lower levels of apoptosis in these cells (Table IV). The stimulation of apoptosis by DMF10.62.3 appears to be independent of fas, as E710.2.3 and RMA-S cells do not express fas (Table IV).

TABLE IV

| | % Apoptotic cells | | | | | |
|---|---|---|---|---|---|---|
| Cell Line | DMF10.62.3 | Hamster IgG | No treatment | Fluorescence Intensity DMF10.62.3/ Hamster IgG | % cells staining positive for DMF10.62.3 | Staining for murine fas surface expression |
| Mouse T cell lines | | | | | | |
| E710.2.3 | 86.9 | 19.8 | 24.7 | 27.5 | 72.6 | – |
| RMA-S | 69.6 | 12.2 | 14.0 | 14.5 | 60.6 | – |
| CTLL | 36.4 | 14.8 | 16.7 | 8.88 | 51.5 | – |
| RF33.70 | 8.1 | 8.6 | 7.8 | 0.98 | 0.48 | – |
| Mouse B cell lines | | | | | | |
| LB27.4 | 16.8 | 7.1 | 10.8 | 1.48 | 7.0 | + |
| A20 | 16.2 | 13.8 | 12.2 | 3.3 | 24.8 | + |
| Human cell lines | | | | | | |
| JURKAT | 33.9 | 12.6 | 11.8 | 16.18 | 49.2 | ND |
| 143BTK- | 29.7 | 21.1 | 20.5 | 3.8 | 29.5 | ND |

Example 5

DMF10.62.3 Causes Homotypic Aggregation in E710.2.3 and Other Cell Lines

Homotypic aggregation is a biologically active process whereby cells are stimulated to adhere to one another. Aggregation assays were set up as follows.

$10^5$ cells were incubated with various concentrations of DMF10.62.3 or hamster IgG or without antibody in 200 it complete RPMI. To test the effect of inhibitors, $10^5$ cells were preincubated with inhibitor for 30 minutes and then DMF10.62.3 mAb (10 µg/ml) was added in the continued presence of inhibitor for 6 hours. To test the effect of paraformaldehyde on aggregation, cells were fixed in 1% paraforinaldehyde for 10 minutes, washed, and then DMF10.62.3 was added for 6 hours. Aggregation was scored visually. Photomicrographs were taken at 6 hours using a thermoelectrically cooled charged-coupled device (CCD) camera (Princeton Instruments, Trenton, N.J.).

DMF10.62.3 was found to induce homotypic aggregation of E710.2.3 in culture. At 6 hours, significant aggregation was observed with cells treated with 5 µg/ml or more of antibody. In contrast, no aggregation was observed in cultures treated with hamster IgG or medium. This aggregation was blocked by treatment with various agents including cytochalasin B, which disrupted actin microfilaments, trifluoperazine, which inhibits calmodulin dependent processes, Na azide+2 deoxyglucose, which inhibits ATP synthesis, and EDTA which chelates Ca2+ and Mg2+. In contrast, aggregation was not affected by colchicine, which inhibited microtubule formation. The aggregation was also inhibited by incubation at 4° C. and by treatment with paraformaldehyde (Table V). These results indicate that the aggregation is an active process and is not simply agglutination.

TABLE V

| CHEMICAL USED | EFFECT ON CELL | HOMOTYPIC ADHESION |
| --- | --- | --- |
| Cytochalasin B (20 µg/ml) | Cytoskeleton (disrupts actin microfilament integricy | − |
| Colchicine (20 µg/ml) | Inhibits microtubule formation | + |
| Trifluoperazine (20 µM) | Inhibits calmodulin dependent processes | − |
| Na azide (0.1%) + 2-deoxyglucose (5 mM) | Inhibits ATP synthesis | − |
| EDTA (10 mM) | chelates Ca2+ and Mg2+ | − |
| Medium only | CONTROL (no effect) | + |
| 4° C. | | − |
| Paraformaldehyde | | − |

DMF10.62.3 also caused homotypic aggregation of some of the other cell lines (e.g. RMA-S, CTLL) which express the DMF10.62.3 binding protein. However, little aggregation above the background was seen for some other DMF10.62.3 positive cell lines (e.g. Jurkat, LB27.4, A20, 143Btk−). No aggregation was seen with RF33.70, to which DMF10.62.3 does not bind.

The aggregation assay can be used to help determine whether a new antibody is one of the new antitumor antibodies of the invention.

Example 6

DMF10.62.3 Immunoprecipitates a 40 kDa Protein which is not GPI-Linked

To characterize the protein bound by DMF10.62.3, $^{35}$S labeling and immunoprecipitation were preformed as follows. $5 \times 10^6$ E710.2.3 cells were starved for 1 hour in methionine-free medium and then incubated for 2 hours with $^{35}$S methionine at 0.5 mCi/ml. Labeled cells were lysed in immunoprecipitation buffer as described by Townsend et al. ((1990) *J. Immunol.* 146:2235). Clarified lysates were precleared with hamster IgG, immunoprecipitated with DMF10.62.3 bound to Protein-A-sepharose, and analyzed by SDS-polyacrylamide gel electrophoresis on 14% gels. To determine the molecular weight of the DMF10.62.3 binding protein, E170.2.3 cells were labeled for 2 hours with $^{35}$S methionine. Immunoprecipitates from labeled cells were analyzed by SDS-PAGE under reducing conditions.

The mAb DMF10.62.3 immunoprecipitated an approximately 40 kDa protein from E710.2.3 under reducing conditions. The electrophoretic mobility of this protein was not altered under non-reducing conditions. This band was not seen in immunoprecipitates with normal hamster IgG, or in immunoprecipitates with an anti-MHC class I antibody, Y-3. A 40 kDa-protein was also identified in lysates of surface labeled E710.2.3 and RMA-S cells.

Several cell surface molecules such as Thy-1 and Ly-6 A/E are linked to the cell surface via glycosylphoshatidylinositol (GPI) anchors. This surface linkage is sensitive to treatment with PI-PLC. To determine if the protein recognized by DMF10.62.3 was GPI-linked, RMA-S cells which express the protein on the cell surface, were treated with PI-PLC. PI-PLC treatment did not reduce DMF10.62.3 staining but did decrease staining for the, GPI-linked molecule Thy-1; suggesting that the 40 kDa protein recognized by DMF10.62.3 is not anchored to the cell surface by a GPI.

Example 7

The In Vivo Effect of the DMF62.3 Antibody

AKR mice were injected IV or IP with $5 \times 10^6$ syngeneic E710.2.3 tumor cells and received saline or an injection IP of 0.5 mg of control or DMF62.3 antibody on the initial day and again 10 days later. The survival of animals was followed for 50 days (Table VI).

TABLE VI

| Treatment | Survival | Average time to death |
| --- | --- | --- |
| 1. saline | 0% | 35 days |
| 2. control antibody | 0% | 33 days |
| 3. DMF62.3 | 100% | (No deaths) |

DEPOSIT STATEMENT

The hybridoma cell line producing the monoclonal antibody DMF10.62.3, was received by the American Type Culture Collection (ATCC), 10801 University Boulevard, Manassas, Va., on Jul. 20, 1999, and the hybridoma cell lines producing the monoclonal antibodies DMF10.167.4 and DMF10.34.36 were received by the American Type Culture Collection (ATCC), 10801 University Boulevard, Manassas, Va., on Jul. 22, 1999. The hybridomas have been deposited under conditions that assure that access to the hybridomas will be available during the pendency of the patent application disclosing them to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganism, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures plus five years after the last request for a sample from the deposit. The depositor acknowledges the duty to replace the deposit should the depository be unable to furnish a sample when requested, due to the condition of the deposits. All restrictions on the availability to the public of the subject culture deposit will be irrevocably removed upon the granting of a patent disclosing them.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting a tumor cell expressing an antigen recognized by antibody DMF10.62.3 in a subject, the method comprising:
   (a) contacting the tumor cell in the subject with an isolated antibody, or antigen-binding fragment thereof, wherein the antibody is selected from the group consisting of:
      (i) monoclonal antibody DMF10.62.3 produced by hybridoma cell line ATCC No. PTA-377;
      (ii) a chimeric version of antibody DMF10.62.3 comprising the light and heavy chain variable regions of monoclonal antibody DMF10.62.3 and human light and heavy chain constant regions, wherein said chimeric version specifically binds to the antigen to which monoclonal antibody DMF10.62.3 binds; and
      (iii) a humanized version of antibody DMF10.62.3 comprising the complementarity determining regions (CDRs) of monoclonal antibody DMF10.62.3, wherein said humanized version specifically binds to the antigen to which monoclonal antibody DMF10.62.3 binds, under conditions that enable specific binding; and
   (b) detecting any specific binding of the antibody to the tumor cell, wherein binding indicates the presence of a tumor cell in the subject.

2. A method according to claim 1, wherein the antibody or antigen-binding fragment thereof comprises a detectable label.

3. A method according to claim 2, wherein the detectable label is selected from the group consisting of an enzyme, streptavidin, avidin, biotin, a fluorescent material, a luminescent material, a bioluminescent material, an electron dense label, an MRI label, and a radioactive material.

4. A method for detecting a tumor cell expressing an antigen recognized by antibody DMF10.62.3 in a subject, the method comprising:
   (a) contacting a tumor cell isolated from the subject with an isolated antibody, or antigen-binding fragment thereof, wherein the antibody is selected from the group consisting of:
      (i) monoclonal antibody DMF10.62.3 produced by hybridoma cell line ATCC No. PTA-377;
      (ii) a chimeric version of antibody DMF10.62.3 comprising the light and heavy chain variable regions of monoclonal antibody DMF10.62.3 and human light and heavy chain constant regions, wherein said chimeric version specifically binds to the antigen to which monoclonal antibody DMF10.62.3 binds; and
      (iii) a humanized version of antibody DMF10.62.3 comprising the complementarity determining regions (CDRs) of monoclonal antibody DMF10.62.3, wherein said humanized version specifically binds to the antigen to which monoclonal antibody DMF10.62.3 binds, under conditions that enable specific binding; and
   (b) detecting any specific binding of the antibody to the tumor cell, wherein binding indicates the presence of a tumor cell in the subject.

5. A method according to claim 3, wherein the enzyme is horseradish peroxidase, alkaline phosphatase, β-galactosidase or acetylcholineasterase.

6. A method according to claim 3, wherein the fluorescent material is umbelliferone, fluorescein, fluorescein isothiocyanate, rhodamine, dichlorotriazinylamine fluorescein, dansyl chloride or phycoerythrin.

7. A method according to claim 3, wherein the radioactive material is $^{125}I$, $^{131}I$, $^{35}S$ or $^{3}H$.

8. A method according to claim 1, wherein the antigen-binding fragment is an F(ab), F(ab')2 or Fv fragment.

9. A method according to claim 2, wherein the antigen-binding fragment is an F(ab), F(ab')2 or Fv fragment.

10. A method according to claim 2, wherein the tumor cell is selected from the group consisting of thymic lymphoma, a T cell tumor, a B cell lymphoma, melanoma, osteosarcoma, and acute T cell leukemia.

11. A method according to claim 2, wherein bound antibody is detected using external scintigraphy, emission tomography or radionuclear scanning.

12. The method of claim 4, wherein the antibody or antigen-binding fragment thereof comprises a detectable label.

13. The method of claim 12, wherein the detectable label is selected from the group consisting of an enzyme, streptavidin, avidin, biotin, a fluorescent material, a luminescent material, a bioluminescent material, an electron dense label, an MRI label, and a radioactive material.

14. A method according to claim 13, wherein the enzyme is horseradish peroxidase, alkaline phosphatase, β-galactosidase or acetylcholineasterase.

15. A method according to claim 13, wherein the fluorescent material is umbelliferone, fluorescein, fluorescein isothiocyanate, rhodamine, dichlorotriazinylamine fluorescein, dansyl chloride or phycoerythrin.

16. A method according to claim 13, wherein the radioactive material is $^{125}I$, $^{131}I$, $^{35}S$ or $^{3}H$.

17. A method according to claim 4, wherein the antigen-binding fragment is an F(ab), $F(ab')_2$ or Fv fragment.

18. A method according to claim 12, wherein the antigen-binding fragment is an F(ab), $F(ab')_2$ or Fv fragment.

19. A method according to claim 12, wherein the tumor cell is selected from the group consisting of thymic lymphoma, a T cell tumor, a B cell lymphoma, melanoma, osteosarcoma, and acute T cell leukemia.

* * * * *